United States Patent [19]

Rosenthaler

[11] 4,240,789
[45] Dec. 23, 1980

[54] DENTAL APPLIANCE

[76] Inventor: Harold B. Rosenthaler, 8201 Henry Ave., Apt. P25, Philadelphia, Pa. 19128

[21] Appl. No.: 941,458

[22] Filed: Sep. 12, 1978

[51] Int. Cl.³ .......................... A61C 5/14; A61C 17/04
[52] U.S. Cl. ...................................... 433/136; 433/91; 433/93
[58] Field of Search .............. 32/33, 34, 35; 433/136, 433/93, 91

[56] References Cited

U.S. PATENT DOCUMENTS

| | | | |
|---|---|---|---|
| 1,292,133 | 1/1919 | Stoughton | 32/35 |
| 1,596,478 | 8/1926 | Bittenbender | 32/33 |
| 3,396,468 | 8/1968 | Dayhoff | 32/33 |
| 3,406,452 | 10/1968 | McConville | 32/35 |
| 3,735,491 | 5/1973 | Pabalan, Jr. | 32/33 |
| 3,781,994 | 1/1974 | Hesselgren | 32/35 |

*Primary Examiner*—Robert Peshock
*Assistant Examiner*—John J. Wilson
*Attorney, Agent, or Firm*—Walter B. Udell

[57] ABSTRACT

A hollow U-shaped rubber dam device which eliminates the need for a dental assistant to handle a suction tube to maintain a dry field of work and prevent water from a dental drill from running uncontrollably over the patient by providing a structure which by itself maintains a dry field for dental work. The device is constructed so as to provide a suction path through the hollow interior for connection to the standard suction coupling of a dental stand, and to accept the standard dental suction tube fitting as an easily attachable and detachable part. The hollow interior suction path includes means for cleaning out and sterilizing the interior passages formed within a portion of the body of the device. The device is suitably made of radio-transparent material, such as molded plastic, and may remain in place while X-rays are taken without producing shadows on the exposed X-ray film.

14 Claims, 7 Drawing Figures

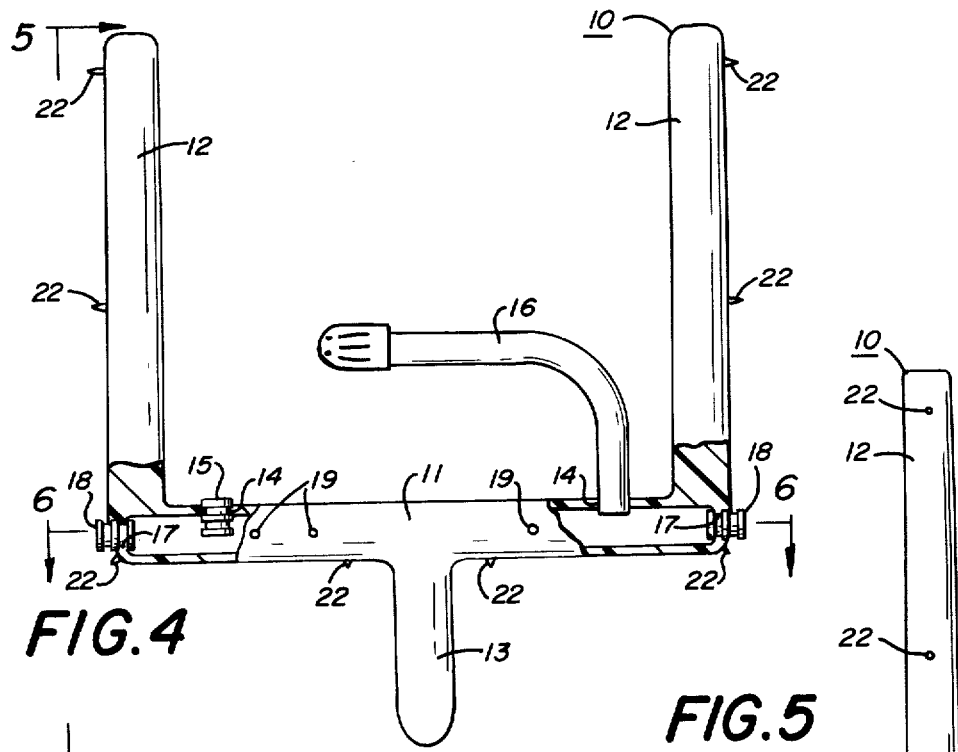
FIG.4
FIG.5
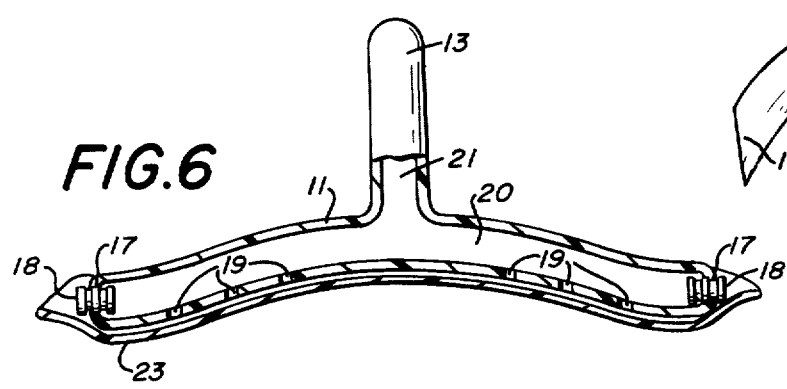
FIG.6
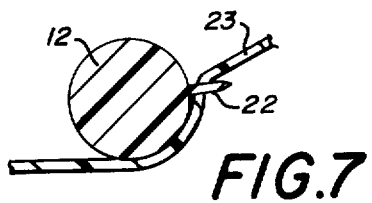
FIG.7

DENTAL APPLIANCE

This invention relates generally to dental appliances, and more particularly relates to a novel rubber dam device.

In the past, rubber dam frames have been well known in dental use for maintaining a dry field for dental work in progress and to prevent dental debris from entering the patient's mouth and throat. The conventional type of rubber dam structure utilizes a U-shaped metal frame to which a piece of rubber sheeting is attached which then becomes the dam, the rubber sheeting being first perforated for projection of the teeth therethrough, and then clamped around the tooth or teeth to be worked upon. The high speed dental drill uses water as a cooling medium for the tooth and causes a considerable water discharge over the face of the dam which necessitates the use of a suction tube handled by a dental assistant to maintain a dry field of work and prevent the water from running uncontrollably over the patient.

The rubber dam device according to the invention eliminates the need for a dental assistant to handle the suction tube by providing a structure which by itself maintains a dry field for dental work. Accordingly, the dental assistant may either be dispensed with, or may be utilized for other purposes during the dental procedure.

Briefly, the rubber dam device according to the invention is constructed so as to provide a suction path for connection to the standard suction coupling of a dental stand, and to accept the standard dental suction tube fitting as an easily attachable and detachable part. Additionally, most, although not all, rubber dam frames heretofore utilized have been made of metal which is radio-opaque, and which cast shadows on X-ray films if such are exposed during the course of the dental procedure with the rubber dam frame in position. In the past, this has sometimes required the removal of the rubber dam structure at an intermediate point in the dental procedure in order to take X-rays for the purpose of checking the course of the procedure, followed by the necessity for reinstalling the rubber dam structure. This problem is eliminated by the rubber dam device according to the invention which is suitably made of radio-transparent material, such as molded plastic, and which may remain in place while X-rays are taken without producing shadows on the exposed X-ray film.

A primary object of the invention is the provision of a novel dental rubber dam device which incorporates within its structure means for applying suction to the field of work without the intermediary agency of a dental assistant.

Another object of the invention is to provide a novel rubber dam device as aforesaid which is radio-transparent and may remain in operative installed position during the entire course of a dental procedure without adversely affecting dental X-rays taken during the course of the dental procedure.

A further object of the invention is to provide a novel rubber dam device as aforesaid which incorporates provisions for the use of a standard dental suction tube by operative connection to the device at a plurality of locations, and which includes means for cleaning out and sterilizing the interior suction passages formed within a portion of the body of the device.

The foregoing and other objects of the invention will become clear from a reading of the following specification in conjunction with an examination of the appended drawings, wherein:

FIG. 4 is a view of the rubber dam device from the side of the frame which in use is closest to the patient's face, portions being sectioned away to disclose interior details;

FIG. 5 is a side view of the rubber dam device as would be seen when viewed along the line 5—5 of FIG. 4;

Figure 3:
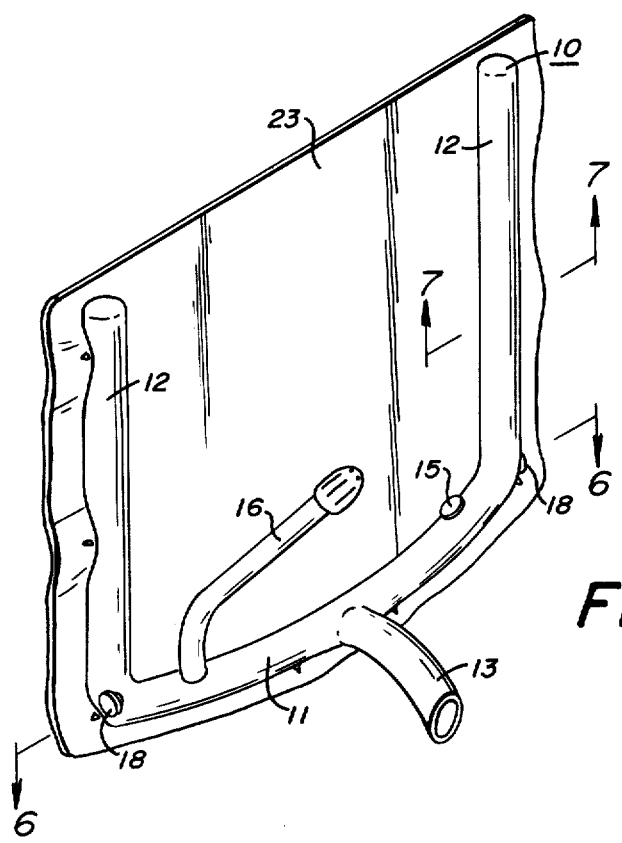
FIG. 3 is a perspective view of the rubber dam device according to the invention with a sheet of rubber and a suction tube installed.

FIG. 6 is a horizontal sectional view through the rubber dam device as would be seen when viewed along the lines 6—6 of FIGS. 3 and 4; and FIG. 7 is a horizontal section through one of the arms of the rubber dam device, on an enlarged scale, as would be seen when viewed along the lines 7—7 of FIG. 3.

In the several figures, like elements are denoted by like reference characters.

Turning now to the drawings, it is observed that the rubber dam device according to the invention is designated generally as 10, having a horizontal lower arm 11 from the opposite ends of which upwardly extend a pair of vertical side arms 12, and from the center of which downwardly extends a suction stem 13. As best seen from FIGS. 4 and 6, the suction stem 13 and the horizontal arm 11 are hollow and interconnected so that suction applied at the end of the stem 13 is also applied within the hollow branches of the horizontal arm 11. The upper surface of the arm 11 is provided, at a point spaced somewhat in from the ends thereof, with openings 14, within one of which openings is disposed a sealing rubber plug 15, and within the other of which openings is seated a standard disposable dental suction tube 16. The opposite ends of the horizontal arm 11 are also apertured as at 17, and the apertures are closed by sealing rubber plugs 18. Additionally, formed through the vertical surface of the horizontal arm 11 which faces the patient are a plurality of apertures 19 which communicate with the hollow interior 20 of horizontal arm 11, which in turn communicates with the hollow interior 21 of suction stem 13.

Figure 1:
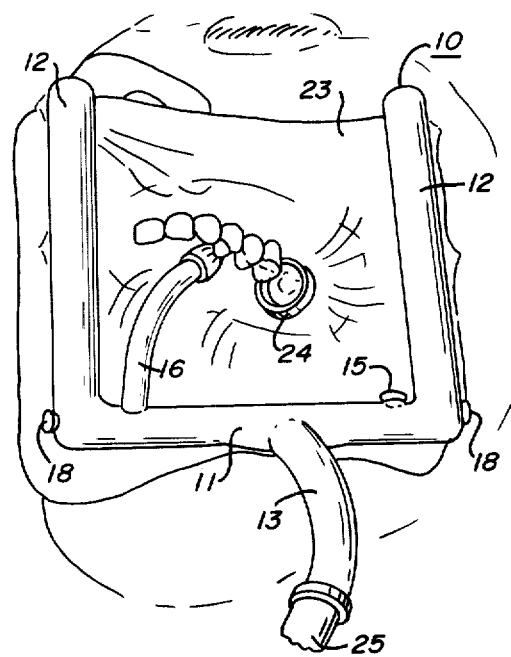
FIG. 1 is a perspective view of the dental rubber dam device according to the invention in operative position installed upon the teeth of a dental patient.

Formed on the outwardly facing side of the vertical arms 12 and the bottom surface of horizontal arm 11 and at the corner junctions of the vertical and horizontal arms are a plurality of prongs 22 which pierce through and retain a rubber membrane 23 in taut stretched condition on the frame 10. As best seen in FIG. 1, the membrane 23 is slit and stretched to contract about the teeth of a person being worked upon and the rubber membrane is clamped to a tooth by a standard clamp 24 which holds the entire rubber dam structure on the face of the patient.

The suction tube 16, being deformable, is bent over into the proper position to aspirate water and debris resulting from the drilling operation through its hollow interior into the hollow interior 20 of arm 11, and then down through suction stem 13 into the suction apparatus of the dental stand via the connection to the dental stand suction coupling 25. Any water which is not picked up by the suction tube 16 flows down over the face of the rubber membrane 23 and is drawn into the hollow interior of arm 11 through the arm apertures 19. The disposable suction tube 16 may be plugged into either of the openings 14 in the arm 11 as a function of the desired positioning of the suction tube with respect to the teeth being worked upon, the other opening 14 then being sealed with the rubber plug 15.

For cleaning and sanitizing purposes, the suction tube 16 is removed, as are the rubber plugs 15 and 18, thus permitting a cleaning brush to be run through the horizontal arm 11 from end to end. Additionally, the entire frame 10 is autoclavable to sterilize the interior passages 20 and 21.

Figure 2:
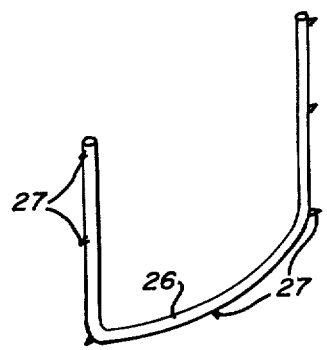
FIG. 2 is an illustration of the prior art type of dental rubber dam frame.

The typical prior art device shown in FIG. 2 is a solid piece of material 26 provided with prongs 27 which function in the same manner as the prongs 22 of the invention. This prior art structure does not have the ability to maintain a dry field because it cannot provide the suction function, and requires the attendance of a dental assistant to manipulate a suction tube.

Having now described my invention in connection with a particularly illustrated embodiment thereof, variations and modifications of the invention may now naturally occur to those persons normally skilled in the art without departing from the essential scope or spirit of the invention, and accordingly it is intended to claim the same broadly as well as specifically as indicated by the appended claims.

What is claimed to be new and useful is:

1. A rubber dam device for dental use comprising in combination,
   (a) a frame including means for detachably carrying a rubber dam membrane, said means being located on said frame so that in use the rubber dam membrane is disposed between said frame and the face of a dental patient, said frame being of a size and shape requiring that it be external to the mouth of a dental patient,
   (b) support means for supporting a suction tube from said frame so that one end of the suction tube is free for variable positioning,
   (c) a suction tube operatively coupled to said suction tube support means, and
   (d) means for connecting a suction source to the suction tube when the latter is operatively supported by said support means.

2. A rubber dam device as set forth in claim 1 wherein said suction tube support means is an integral part of said frame.

3. A rubber dam device as set forth in claim 1 wherein said suction tube support means is an integral part of said frame, said dam device further including
   (a) a hollow passage through at least a portion of said frame,
   (b) means for connecting one open end of the suction tube to the frame so that it communicates with the said hollow passage.

4. A rubber dam device as set forth in claim 1 wherein said suction tube support means is an integral part of said frame, said dam device further including
   (a) a hollow passage through at least a portion of said frame,
   (b) means for connecting one open end of the suction tube to the frame so that it communicates with the said hollow passage, and
   (c) a plurality of spaced apart apertures into said hollow passage from the outside of said frame, said apertures being located to receive fluid which flows over the surface of the rubber dam membrane and escapes pick-up by the suction tube.

5. A rubber dam device as set forth in claim 4 further including
   openable and closable access ports entering into said hollow passage at locations permitting the entire said passage to be cleaned.

6. A rubber dam device as set forth in claim 1 wherein said suction tube support means is an integral part of said frame, said dam device further including
   (a) a hollow passage through at least a portion of said frame,
   (b) means for connecting one open end of the suction tube to the frame so that it communicates with the said hollow passage, and
   (c) openable and closable access ports entering into said hollow passage at locations permitting the entire said passage to be cleaned.

7. A rubber dam device for dental use comprising in combination,
   (a) a U-shaped frame having a horizontal arm and a pair of vertical arms, one of said pair of vertical arms extending upward from one end of said horizontal arm and the other of said pair of vertical arms extending upward from the other end of said horizontal arm,
   (b) said horizontal arm having
      (1) a hollow passage therethrough substantially from one end to the other,
      (2) means for connecting one open end of a dental suction tube to said horizontal arm so that it communicates with the said passage therethrough,
      (3) a plurality of spaced apart apertures through said horizontal arm from the said passage to the outside surface which when the dam device is in use faces the patient,
   (c) a hollow suction stem, one open end of which connects to said horizontal arm and communicates with the said horizontal arm hollow passage, and the other end of which is adapted for connection to the suction coupling of a dental stand,
   (d) means carried by said vertical and horizontal arms for detachably holding a rubber dam membrane in operative position.

8. A rubber dam device as set forth in claim 7 further including openable and sealable access ports into said horizontal arm entering into opposite ends of said hollow passage to permit cleaning of the walls of said passage.

9. A rubber dam device as set forth in claim 7 wherein said means for connecting one open end of a dental suction tube to said horizontal arm are plural and spaced apart along said horizontal arm, those of said spaced apart means which at a given time are not connected to a suction tube being sealed by openable and closable sealing means.

10. A rubber dam device as set forth in claims 1 or 7 wherein said device is made of radio-transparent material.

11. A rubber dam device for dental use comprising in combination,
   (a) a frame including a hollow passage through at least a portion thereof and also including means for detachably carrying a rubber dam membrane,
   (b) support means for supporting a suction tube from said frame so that one end of the suction tube is free for variable positioning, said suction tube support means being an integral part of said frame and comprising a plurality of separate spaced apart means for connecting one open end of the suction tube selectively to the frame so that it communicates with the said hollow passage, those of the spaced apart means for connecting the suction tube to the frame which at a given time are not so connected being sealed by openable and closable sealing means, and (c) means for connecting a suction source to the suction tube when the latter is operatively supported by said support means.

12. A device as set forth in claim 11 wherein said means for connecting a suction source to the suction tube comprises a hollow open ended suction stem one end of which communicates with the said hollow passage and the other end of which is adapted for connection to the suction coupling of a dental stand.

13. A rubber dam device for dental use comprising in combination, (a) a frame including a hollow passage through at least a portion thereof and also including means for detachably carrying a rubber dam membrane, (b) support means for supporting a suction tube from said frame so that one end of the suction tube is free for variable positioning, said suction tube support means being an integral part of said frame and comprising a plurality of separate spaced apart means for connecting one open end of the suction tube selectively to the frame so that it communicates with the said hollow passage, those of the spaced apart means for connecting the suction tube to the frame which at a given time are not so connected being sealed by openable and closable sealing means, (c) a plurality of spaced apart apertures into said hollow passage from the outside of said frame, said apertures being located to receive fluid which flows over the surface of the rubber dam membrane and escapes pick-up by the suction tube, and (d) means for connecting a suction source to the suction tube when the latter is operatively supported by said support means.

14. A rubber dam device as set forth in claim 13 further including openable and closable access ports entering into said hollow passage at locations permitting the entire said passage to be cleaned.

* * * * *